United States Patent [19]

Blewett

[11] Patent Number: 5,480,089
[45] Date of Patent: Jan. 2, 1996

[54] SURGICAL STAPLER APPARATUS WITH IMPROVED STAPLE POCKETS

[75] Inventor: Jeffrey J. Blewett, Plantsville, Conn.

[73] Assignee: United States Surgical Corporation, Norwalk, Conn.

[21] Appl. No.: 293,235

[22] Filed: Aug. 19, 1994

[51] Int. Cl.⁶ .................................................. A61B 17/068
[52] U.S. Cl. ........................................ 227/175.1; 227/19
[58] Field of Search .......................... 227/19, 175, 119, 227/107, 134, 155, 902

[56] References Cited

U.S. PATENT DOCUMENTS

| | | |
|---|---|---|
| 2,073,960 | 3/1937 | Crosby . |
| 2,487,565 | 11/1949 | Leber et al. . |
| 3,490,675 | 1/1970 | Green et al. ................................ 227/19 |
| 3,494,533 | 2/1970 | Green et al. . |
| 3,499,591 | 3/1970 | Green ......................................... 227/19 |
| 4,281,785 | 8/1981 | Brooks . |
| 4,508,253 | 4/1985 | Green . |
| 4,520,817 | 6/1985 | Green . |
| 4,632,290 | 12/1986 | Green et al. . |
| 4,767,044 | 8/1988 | Green ......................................... 227/19 |
| 5,040,715 | 8/1991 | Green et al. . |
| 5,111,987 | 5/1992 | Moeinzadeh et al. ...................... 227/19 |
| 5,119,983 | 6/1992 | Green et al. . |
| 5,318,221 | 6/1994 | Green et al. . |
| 5,350,400 | 9/1994 | Esposito et al. . |

FOREIGN PATENT DOCUMENTS 0251444  1/1988  European Pat. Off. .

*Primary Examiner*—Scott A. Smith

[57] ABSTRACT

An apparatus is disclosed for driving one or more U-shaped surgical staples through body tissue and against an anvil to deflect, crimp, or clinch the ends of the staple legs and thereby secure the tissue. The apparatus has an anvil with a plurality of staple pockets in the surface of the anvil. Each staple pocket has a first and a second staple leg forming cup. At least one channeling surface is disposed around a perimeter of each of the staple leg forming cups to guide the staple legs into the staple leg forming cups. The channeling surfaces have a substantially lemniscate shape.

15 Claims, 5 Drawing Sheets

SURGICAL STAPLER APPARATUS WITH IMPROVED STAPLE POCKETS

BACKGROUND

1. Technical Field

The technical field relates to surgical staplers, and more particularly to improved anvils for use in surgical staplers of the type in which one or more U-shaped surgical staples are driven through body tissue and against an anvil to deflect, crimp, or clinch the ends of the staple legs and thereby secure the tissue.

2. Background of Related Art

Surgical staplers having a wide variety of configurations are known. In one general type of surgical stapler, the tissue to be stapled is positioned between a staple holding assembly and an opposing anvil assembly, and one or more generally U-shaped staples are driven from the staple holding assembly, through the tissue, and against the anvil to deflect, crimp, or clinch the ends of the legs of the staples and secure the tissue. In relation to forming a staple, the words "deflect", crimp, and "clinch" are used interchangeably herein to refer to deformation of the staple by the anvil. Examples of of surgical staplers having anvils are disclosed in. U.S. Pat. Nos. 4,508,253, 4,520,817, 5,040,715, 5,119, 983 and 5,318,221.

In staplers of the general type described above, it is conventional to provide separate anvil slots at each staple forming location. This makes it necessary to maintain relatively stringent alignment between the staple holding assembly and the anvil to assure that the staples enter the anvil slots correctly for proper clinching. It is important that every staple be formed properly since an incompletely or improperly formed staple may leave a gap in a wound closure. The importance of maintaining good alignment between the relatively movable staple holding assembly and anvil assembly may contribute to the complexity of the instrument and to the cost of manufacturing and maintaining it.

SUMMARY

An anvil for use with surgical staplers is provided in which the staple crimping surface of the anvil assembly has a plurality of staple pockets each having first and second staple leg forming cups. Each of the staple forming cups is supplemented about its periphery by at least one channeling surface formed in the surface of the anvil. Each channeling surface has a slope different than that of the staple leg forming cup(s) that it surrounds. The anvil is configured such that respective staple legs of the staple initially contact the channeling surface wherein the staple legs are directed into the staple leg forming cups of the staple pockets.

In one embodiment, each staple leg forming cup has a cross section surface forming an arc having a radius R. The staple leg forming cups are configured to receive a staple made of round wire having a radius r, wherein the radius R is in the range of 1.0 r to 2.0 r.

BRIEF DESCRIPTION OF THE DRAWINGS

Various embodiments are described herein with reference to the drawings, wherein.

DETAILED DESCRIPTION OF PREFERRED EMBODIMENTS

Figure 1:
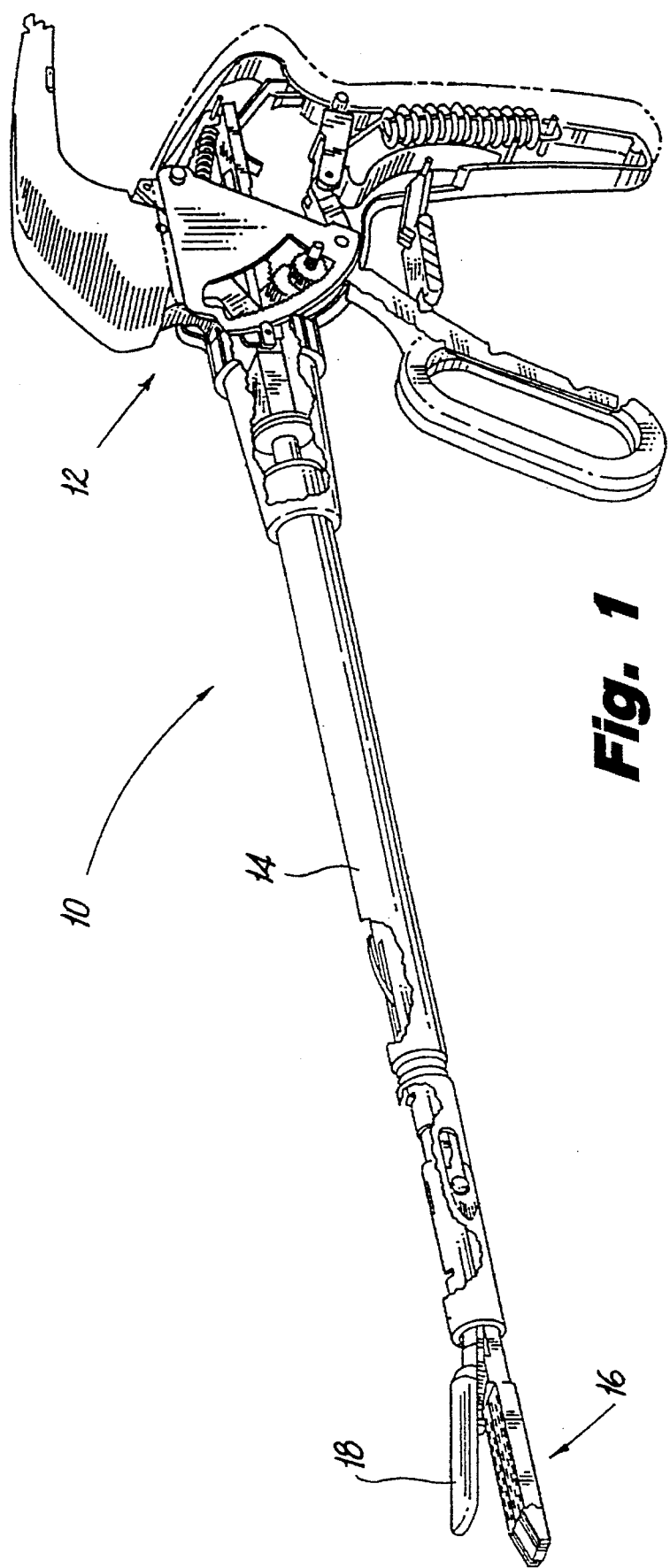
FIG. 1 illustrates a perspective view of a surgical stapling apparatus for use with the anvil member.

FIG. 1 illustrates a typical linear closure surgical stapler of the type shown, for example, in Green et al. U.S. Pat. No. 5,318,221. The particular configuration of the stapler is not critical to the present invention, and the stapler shown serves only to illustrate one possible environment for the invention. The invention can be utilized in other linear staplers, such as those described in U.S. Pat. Nos. 4,508,253, 4,520,819, and in circular staplers, such as that disclosed in U.S. Pat. No. 5,119,983.

As is now well known to those skilled in the art, the stapler 10 shown in FIG. 1 includes an endoscopic portion 14 extending longitudinally from frame 12. The distal end of endoscopic portion 14 holds a cartridge assembly 16 and an anvil member 18.

Figure 2:
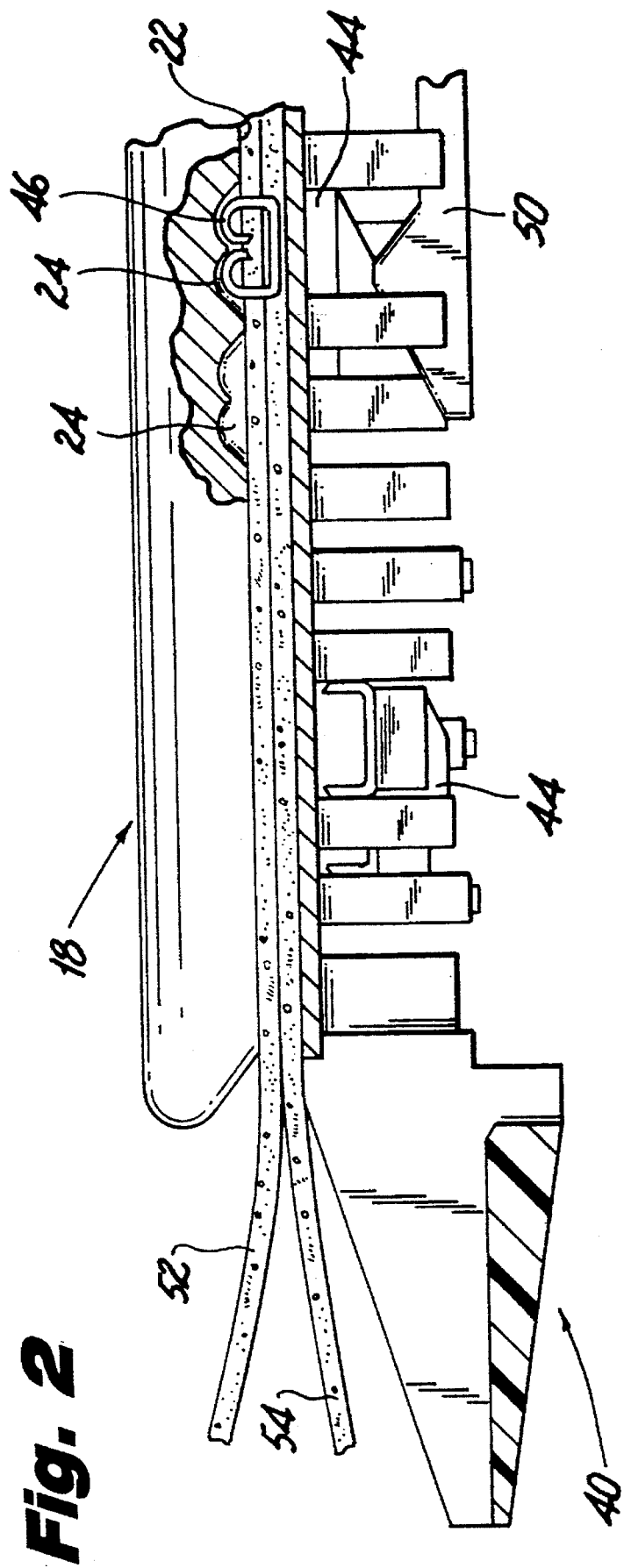
FIG. 2 illustrates a side view in partial cross section of the cartridge and anvil structure.

Referring to FIG. 2, anvil member 18 is an elongated piece having a tissue contacting surface 22 and staple pockets 24 formed therein. Anvil member 18 is pivotable between an open position, and a closed position where the anvil forming surface is brought into close cooperative alignment with the cartridge assembly 16. Anvil member 18 provides one of the jaws of the instrument for clamping and securing the body tissue to be fastened.

Cartridge assembly 16 comprises a cartridge 40 with pusher elements or staple drivers 44, and surgical fasteners or staples 46. The staples 46 and staple drivers 44 are disposed such that as the cam bars 50 move distally and longitudinally through cartridge 40, staple drivers 44 drive staples 46 through body tissue layers 52 and 54 which are to be joined, and against anvil member 18 where the legs of the staples are crimped in staple pockets 24.

Figure 3:
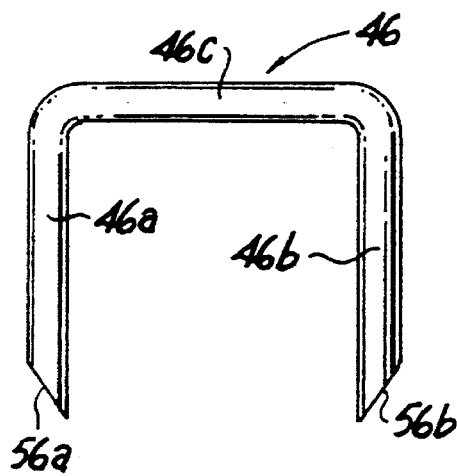
FIG. 3 is a frontal view of a staple of the type formed by one of the staple pockets of the anvil.

As best seen in FIG. 3, each staple 46 is typically preformed in the shape of a square cornered U. Each staple 46 includes two initially straight, substantially parallel legs 46a and 46b which are joined together at one end by base 46c. Legs 46a and 46b are typically at right angles to base 46c, and the free ends 56a and 56b are typically sharply pointed to facilitate penetration of the tissue to be stapled. Staple 46 is typically made of a round metal wire, although other cross-sectional shapes such as square or rectangular shapes are possible and are within the scope of this invention.

Although not necessary to an understanding of the present invention, additional information regarding the construction and operation of staplers of the type shown in FIG. 1 and described above will be found in Green et al. U.S. Pat. Nos. 5,040,715 and 5,318,221.

Figure 6:
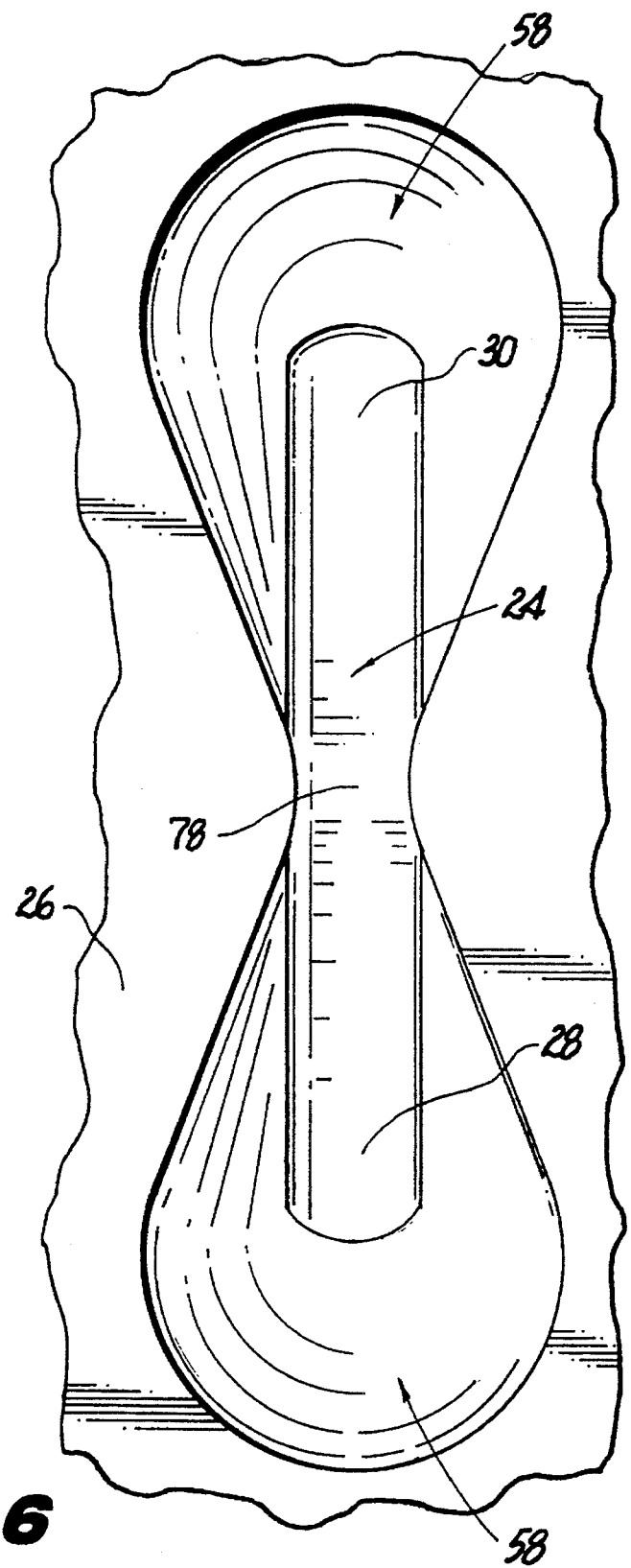
FIG. 6 is a top plan view of the staple pocket of FIG. 5.
Figure 4:
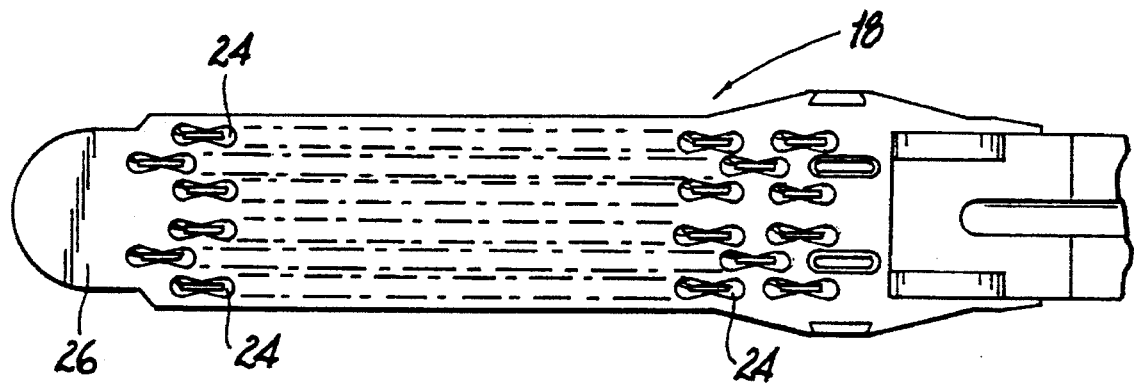
FIG. 4 is a bottom plan view of the anvil member of FIG. 1 illustrating a preferred embodiment of the array of staple pockets.
Figure 5:
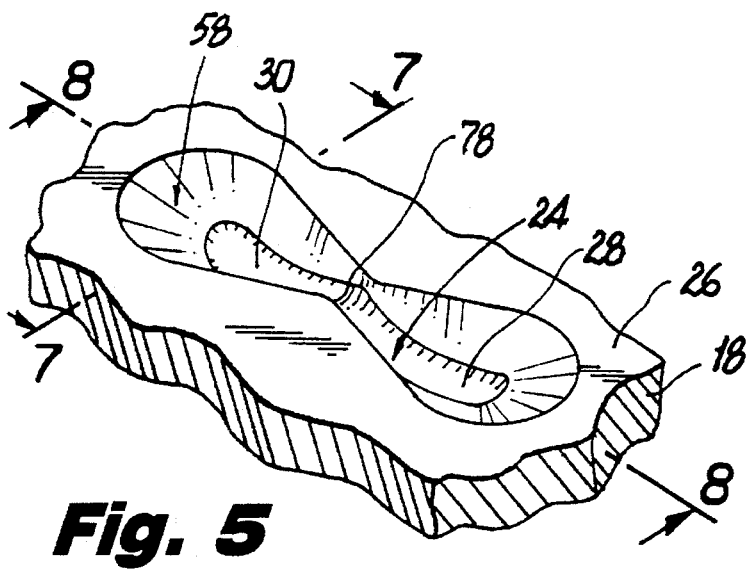
FIG. 5 is a partial perspective view of the anvil member of FIG. 4 illustrating a single staple pocket.
Figure 7:
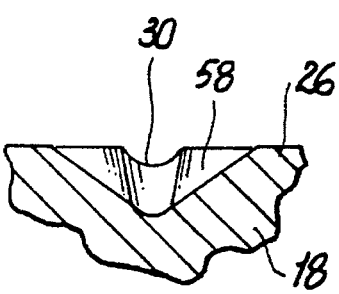
FIG. 7 is a view taken along lines 7—7 of FIG. 5 illustrating the staple pocket.
Figure 8:
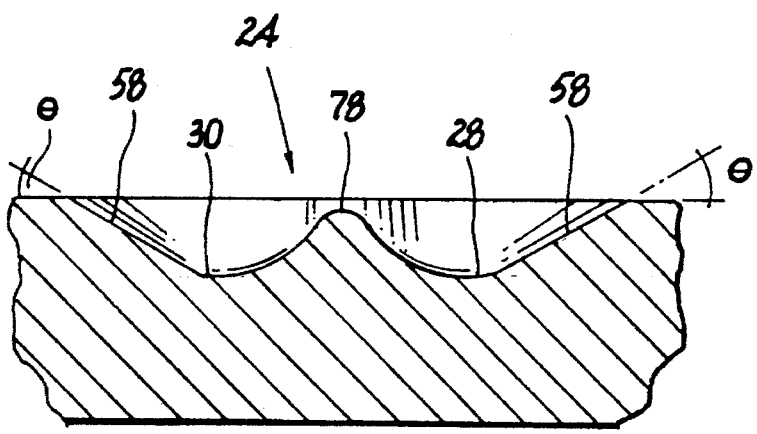
FIG. 8 is a view taken along lines 8—8 of FIG. 5 illustrating the height characteristics of the staple pocket.

In accordance with the present invention, the staple channeling and clinching surfaces of anvil member 18 will now be described with reference to FIGS. 4–8. Anvil member 18 has a substantially flat upper surface 26 having a plurality of staple pockets 24 formed therein. Each staple pocket 24 has a first staple leg forming cup 28 and a second staple leg forming cup 30 for forming respective legs of a staple. Preferably, as shown in FIG. 6, staple leg forming cups 28 and 30 are symetrical about intermediate point 78. As best seen in FIGS. 6 and 8, a substantially lemniscate (figure-eight shaped curve) channeling surface 58 is also formed in the flat upper surface 26 around a perimeter of staple pocket 24. Channeling surface 58 forms an angle Ø, with respect to a plane defined by flat upper surface 26, wherein 0°<Ø<90°. Each staple forming cup 28, 30 has a different slope than that of adjacent channeling surface 58.

Figure 9:
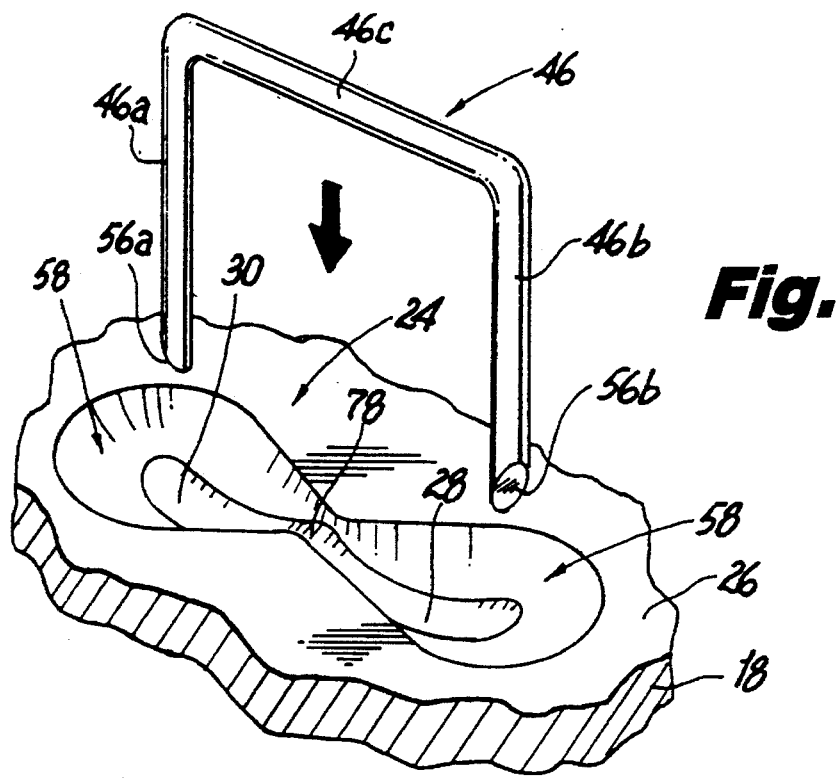
FIG. 9 is a view similar to that of FIG. 5 illustrating a staple prior to formation by the staple pocket.
Figure 10:
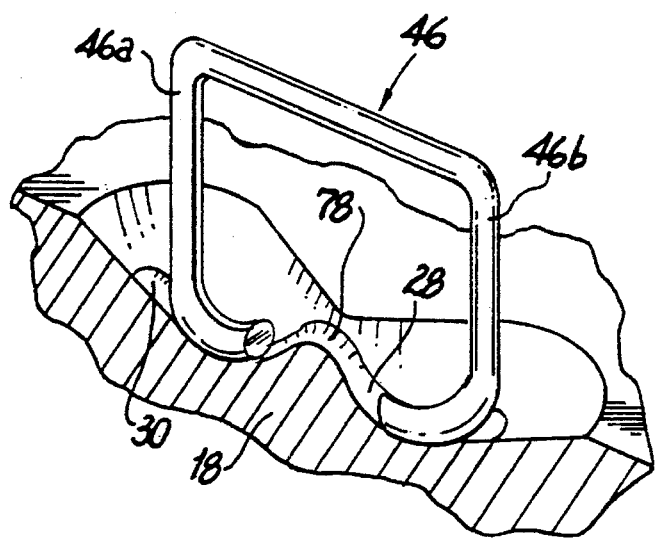
FIG. 10 is a view similar to that of FIG. 9 illustrating the staple partially formed by the staple pocket.
Figure 11:
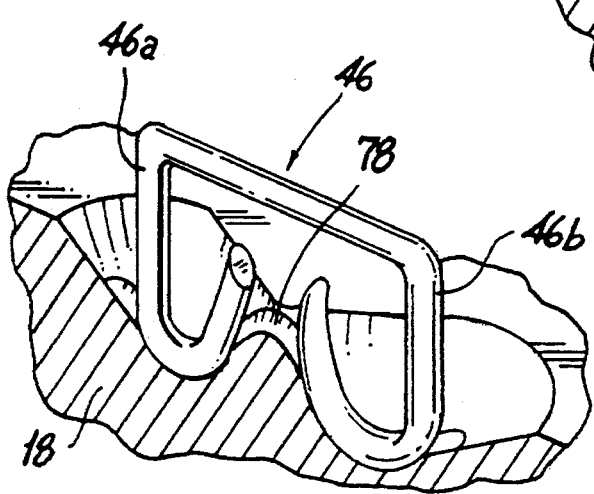
FIG. 11 is a view similar to that of FIG. 10 illustrating the staple fully formed by the staple pocket.

Referring to FIGS. 9–11, the first and second staple leg forming cups 28, 30 of staple pockets 24 are shaped to promote bending of staple legs 46a and 46b in a desired manner when staple 46 is driven against staple pocket 24. Channeling surface 58 is shaped so that free ends 56a and 56b of staple legs 46a and 46b are guided respectively toward first and second staple leg forming cups 28 and 30 of staple pocket 24 as best seen in FIG. 10. As staple 46 is further driven toward anvil member 18 as seen in FIGS. 10–11, staple legs 46a and 46b are directed within first and second staple leg forming cups 28 and 30 toward intermediate point 78 and simultaneously formed by the surface contours of first and second staple leg forming cups 28 and 30.

The provision of channeling surface 58 disposed around a perimeter of staple pocket 24 relaxes the tolerances of the surgical stapler required for aligning cartridge assembly 16 with anvil member 18. The relative location of insertion of staple legs 46a and 46b, respectively, into staple pocket 24 is not critical as legs 46a and 46b will always be guided by channeling surface 58 into respective staple leg forming cups 28, 30 so that the proper finished staple will be formed. The requirement for precise alignment of staple legs 46a and 46b is reduced, and staple pocket 24 eases clearance and tolerance requirements for many parts of the surgical stapler. This in turn substantially reduces the cost of the apparatus and facilitates manufacture and maintenance of the apparatus.

Figure 12:
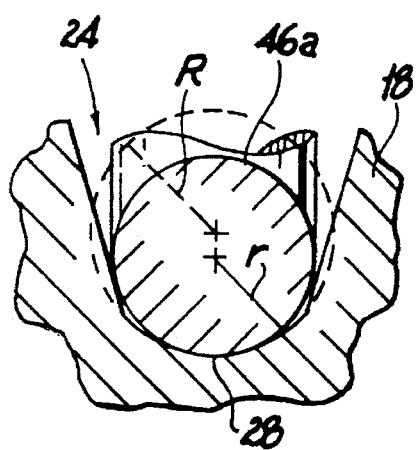
FIG. 12 is a cross-sectional view of a staple leg disposed within an alternative embodiment of a staple leg forming cup.

In a preferred embodiment the staple is made of round wire as shown in FIG. 12. The round wire has a radius "r" and the cross section surface of first staple leg forming cup 28 is an arc of circle having a radius "R". "R" is in the range from 1.0 r to 2.0 r, preferably in the range of from 1.0 r to 1.5 r.

It will be understood that various modifications may be made to the embodiments disclosed herein. For example, the value of "R" may decrease progressively from the ends of the staple leg forming cups to a minor value at the intermediate point while "r" is equal to 1.5 r at the proximal and distal ends while being only 1.2 r at the intermediate point. Also, for example, the staple pockets can be shaped in a manner other than a lemniscate, such as an oval, rectangle, circle or hourglass shape.

Therefore, the above description should not be construed as limiting, but merely as exemplifications of preferred embodiments. Those skilled in art will envision other modifications within the scope and spirit of the claims appended hereto.

What is claimed is:

1. In a staple forming anvil of a surgical stapler, the anvil including a multiplicity of staple forming pockets having proximal end distal ends and defining first and second staple leg forming cups, the improvement comprising a channeling surface formed along a proximal and a distal perimeter portion of each of the staple forming pockets, the channeling surface forming a substantially lemniscate shape.

2. The staple forming anvil defined in claim 1 wherein each of the channeling surfaces has a slope relative to a vertical axis different than a slope relative to said vertical axis of each staple forming pocket.

3. The staple forming anvil defined in claim 1 wherein the anvil has an upper surface defining a horizontal plane, and wherein each of the channeling surfaces defines a plane forming an angle Ø with the horizontal plane wherein 0°<Ø<90°.

4. The staple forming anvil defined in claim 1 wherein the channeling surface adjacent each of the staple forming pockets is symmetrical about at least one axis.

5. The staple forming anvil defined in claim 1 wherein the channeling surface adjacent each of the staple forming pockets is symmetrical about an intermediate point between the first and second staple leg forming cups.

6. The staple forming anvil defined in claim 1 wherein the first and second staple leg forming cups have an arcuate cross section surface with a radius of curvature R, and are configured to form a staple made of round wire having a cross section radius r wherein R is in the range of about 1.0 r to about 2.0 r.

7. In a staple forming anvil of a surgical stapler, the anvil including a substantially flat upper portion defining a horizontal plane, a plurality of staple forming pockets/brined in the upper portion, said staple forming pockets having proximal and distal ends and defining first and second staple leg forming cups, the improvement comprising a curved channeling surface formed in the upper portion above said staple forming pockets and extending along a perimeter portion of said staple forming pockets, the channeling surface forming a lemniscate shape and defining a plane extending through the upper and lower vertical boundaries of said channel surface, said plane forming an angle Ø with the horizontal plane of the upper portion wherein 0°<Ø<90°.

8. The staple/brining anvil defined in claim 7 wherein the plane defined by each of the channeling surfaces has a slope relative to a vertical axis which is different than a slope relative to the vertical axis of each staple forming pocket.

9. The staple forming anvil defined in claim 8 wherein the channeling surface adjacent each of the staple forming pockets is symmetrical about an intermediate point between the first and second staple leg forming cups.

10. The staple forming anvil defined in claim 7 wherein the channeling surface extends around the entire peripheral surface of each of the staple forming pockets.

11. A surgical stapler having an anvil for forming a plurality of surgical staples, the anvil having a surface portion having a plurality of staple forming pockets, the staple forming pockets each having a pair of staple legs forming cups, said anvil further including a lemniscate shaped channeling surface positioned above and along a proximal and distal perimeter portion of the staple forming pockets.

12. The surgical stapler anvil defined in claim 11 wherein each of the channeling surfaces has a slope relative to a vertical axis different than a slope relative to said vertical axis of the staple forming pocket.

13. The surgical stapler anvil defined in claim 11 wherein the staple forming pockets are arranged in at least one linear row.

14. A staple forming anvil comprising:

a plurality of staple forming pockets extending below a tissue engaging surface of an anvil, each said staple forming pocket defining a pair of longitudinally aligned staple leg forming cups between a proximal and a distal end thereof; and a channeling surface formed in said anvil between said tissue engaging surface and said staple forming pocket, said channeling surface defining a substantially lemniscate shape and extending along at least said proximal and distal ends of said staple forming pocket.

15. A staple forming anvil as in claim 14 wherein the pair of longitudinally aligned staple leg forming cups have an arcuate cross section surface with a radius of curvature R, and are configured to form a staple made of round wire having a cross section radius r, wherein R is in the range of about 1.0 r to about 2.0 r.

* * * * *